(12) United States Patent
Sanpei et al.

(10) Patent No.: US 11,058,310 B2
(45) Date of Patent: Jul. 13, 2021

(54) PULSE WAVE SENSOR UNIT

(71) Applicant: ADVANTEST CORPORATION, Tokyo (JP)

(72) Inventors: Hirokazu Sanpei, Miyagi-ken (JP); Kohei Kato, Miyagi-ken (JP)

(73) Assignee: ADVANTEST CORPORATION, Tokyo (JP)

( * ) Notice: Subject to any disclaimer, the term of this patent is extended or adjusted under 35 U.S.C. 154(b) by 34 days.

(21) Appl. No.: 15/509,033

(22) PCT Filed: Sep. 2, 2015

(86) PCT No.: PCT/JP2015/075003
§ 371 (c)(1),
(2) Date: Mar. 6, 2017

(87) PCT Pub. No.: WO2016/047408
PCT Pub. Date: Mar. 31, 2016

(65) Prior Publication Data
US 2017/0281028 A1 Oct. 5, 2017

(30) Foreign Application Priority Data

Sep. 24, 2014 (JP) .............................. JP2014-194214

(51) Int. Cl.
*A61B 5/024* (2006.01)
*A61B 5/0245* (2006.01)
(Continued)

(52) U.S. Cl.
CPC ........ *A61B 5/02438* (2013.01); *A61B 5/0245* (2013.01); *A61B 5/6832* (2013.01);
(Continued)

(58) Field of Classification Search
CPC . A61B 5/02438; A61B 5/0245; A61B 5/6832; G01L 9/0054; G01L 23/18
(Continued)

(56) References Cited

U.S. PATENT DOCUMENTS

| 4,951,679 A | 8/1990 | Harada |
| 2006/0047207 A1* | 3/2006 | Itonaga ..................... A61B 5/02 600/500 |

(Continued)

FOREIGN PATENT DOCUMENTS

| CN | 1524490 A | 9/2004 |
| CN | 101547634 A | 9/2009 |

(Continued)

OTHER PUBLICATIONS

Office Action issued in Japan family member Patent Appl. No. 2014-194214, dated Mar. 21, 2017, along with an English translation thereof.
(Continued)

*Primary Examiner* — Daniel L Cerioni
(74) *Attorney, Agent, or Firm* — Greenblum & Bernstein, P.L.C.

(57) ABSTRACT

A pulse wave sensor unit includes a pressure sensor, and an adhesive tape to attach the pressure sensor to a measurement portion to be measured. The pressure sensor includes a diaphragm part, and an annular support part which supports the diaphragm part and has an aperture for allowing the diaphragm part to face the measurement portion, and a closed space is able to be formed between the diaphragm part and the measurement portion by attaching the pressure sensor to the measurement portion using the adhesive tape.

10 Claims, 7 Drawing Sheets

(51) Int. Cl.
*G01L 9/00* (2006.01)
*G01L 23/18* (2006.01)
*A61B 5/00* (2006.01)
*A61B 5/021* (2006.01)

(52) U.S. Cl.
CPC ............ *G01L 9/0054* (2013.01); *G01L 23/18* (2013.01); *A61B 5/02108* (2013.01); *A61B 2562/0247* (2013.01)

(58) Field of Classification Search
USPC ........................................................ 600/500
See application file for complete search history.

(56) References Cited

U.S. PATENT DOCUMENTS

| | | | |
|---|---|---|---|
| 2006/0169049 | A1 | 8/2006 | Matsubara |
| 2008/0030205 | A1 | 2/2008 | Fujii et al. |
| 2009/0209870 | A1 | 8/2009 | Tanabe |
| 2009/0229370 | A1 | 9/2009 | Fujii et al. |
| 2010/0076328 | A1 | 3/2010 | Matsumum et al. |
| 2011/0249853 | A1 | 10/2011 | Jilani et al. |
| 2013/0077215 | A1 | 3/2013 | Tada et al. |
| 2013/0079648 | A1 | 3/2013 | Fukuzawa et al. |
| 2014/0114201 | A1* | 4/2014 | Watanabe ............ H04R 1/2807 600/485 |
| 2014/0257117 | A1* | 9/2014 | Sato .................... A61B 5/02125 600/500 |
| 2014/0303521 | A1 | 10/2014 | Nakamura et al. |
| 2015/0141774 | A1 | 5/2015 | Ogawa et al. |
| 2016/0023245 | A1* | 1/2016 | Zadesky ............... A61B 5/7455 310/334 |

FOREIGN PATENT DOCUMENTS

| | | |
|---|---|---|
| CN | 103025107 A | 4/2013 |
| JP | 1-195843 A | 8/1989 |
| JP | 11-14479 A | 1/1999 |
| JP | 2000-060845 A | 2/2000 |
| JP | 2006-237401 A | 9/2006 |
| JP | 2007-289501 A | 11/2007 |
| JP | 2008-020433 A | 1/2008 |
| JP | 2012-516628 A | 7/2012 |
| JP | 2013-70271 A | 4/2013 |
| JP | 2013-70732 A | 4/2013 |
| JP | 2013-103040 A | 5/2013 |
| JP | 2013-143391 A | 7/2013 |
| JP | 2013-148495 A | 8/2013 |
| JP | 2013-244287 A | 12/2013 |
| JP | 2014-83122 A | 5/2014 |
| JP | 5543036 B1 | 7/2014 |
| WO | 2013-145352 A1 | 10/2013 |
| WO | 2014/021335 A1 | 2/2014 |

OTHER PUBLICATIONS

Office Action issued in Japan family member Patent Appl. No. 2014-194220, dated Mar. 14, 2017, along with an English translation thereof.

Office Action issued in Japan family member Patent Appl. No. 2014-194219, dated Mar. 14, 2017, along with an English translation thereof.

Search Report issued in PCT Patent Application No. PCT/JP2015/075003, dated Nov. 24, 2015.

Office Action issued in China family member Patent Appl. No. 201580047660.8, dated Dec. 24, 2019.

Office Action issued in Chinese Counterpart Patent Appl. No. 201580047660.8 dated Oct. 26, 2020, along with an English translation thereof.

Office Action issued in Chinese Counterpart Patent Appl. No. 201580047660.8, dated Jan. 28, 2021, along with an English translation thereof.

* cited by examiner

PULSE WAVE SENSOR UNIT

TECHNICAL FIELD

The present invention relates to a pulse wave sensor unit including a pressure sensor which has a diaphragm part.

For designated countries which permit the incorporation by reference, the contents described and/or illustrated in Japanese Patent Applications No. 2014-194214 filed on Sep. 24, 2014 is incorporated herein by reference, as a part of the description and/or drawings of the present application.

BACKGROUND ART

A tonometry method has been known as a scheme of continuously measuring a pulse wave (for example, see Patent Document 1 (Paragraph 0002)).

CITATION LIST

Patent Document

Patent Document 1: JP 2007-289501 A

SUMMARY OF THE INVENTION

Problem to be Solved by the Invention

In the above-mentioned tonometry method, a change in internal pressure of an artery is measured while maintaining a state in which the artery is evenly pressed. For this reason, even though a pulse wave may be continuously measured, there has been a problem that measurement for a long time is a burden to a subject and problematic.

An object of the present invention is to provide a pulse wave sensor unit capable of continuously measuring a pulse wave for a long time.

Means for Solving Problem

[1] A pulse wave sensor unit according to the invention includes a pressure sensor, and attaching means to attach the pressure sensor to a measurement portion to be measured, wherein the pressure sensor includes a diaphragm part, and an annular support part which supports the diaphragm part and has an aperture for allowing the diaphragm part to face the measurement portion, and a closed space is able to be formed between the diaphragm part and the measurement portion by attaching the pressure sensor to the measurement portion using the attaching means.

[2] In the invention, the pulse wave sensor unit may include a wiring circuit board on which the pressure sensor is mounted.

[3] In the invention, the pulse wave sensor unit may include connecting means which mechanically and electrically connects the wiring circuit board and the pressure sensor to each other, and the wiring circuit board and the pressure sensor may face each other through the connecting means.

[4] In the invention, a space may be formed between the diaphragm part and the wiring circuit board.

[5] In the invention, the space may be formed by the connecting means.

[6] In the invention, the pressure sensor may include a piezo-resistor which is provided in the diaphragm part, and a first electrode which is provided on a first main surface of the support part facing the wiring circuit board and is electrically connected to the piezo-resistor, the wiring circuit board may include a second electrode which is provided on a second main surface facing the pressure sensor, and the connecting means may include connecting parts which connect the first electrodes and the second electrodes.

[7] In the invention, the connecting part may be formed by a solder ball, and the solder ball may include a core, and a solder layer which covers the core.

[8] In the invention, the pulse wave sensor unit may include a cable which has one end connected to the wiring circuit board, and a connector which is connected to the other end of the cable.

[9] In the invention, the wiring circuit board may include a third electrode which is provided on an opposite surface to the second main surface, and a conduction path which electrically connect the second electrode and the third electrode to each other, and the cable may be connected to the third electrode.

[10] In the invention, the pulse wave sensor unit may include an annular seal member which is able to be interposed between the pressure sensor and the measurement portion.

[11] In the invention, the attaching means may be able to attach the pressure sensor to the measurement portion by pressing the pressure sensor against the measurement portion.

[12] In the invention, the pressure sensor may be mounted on the wiring circuit board so that the diaphragm part is positioned on the wiring circuit board side and the aperture is open toward an opposite side to the wiring circuit board.

[13] In the invention, the wiring circuit board may have a through-hole or a depression which faces the diaphragm part.

[14] In the invention, the connecting part may be formed by a solder ball or a conductive adhesive.

[15] In the invention, the seal member may stick to the support part.

Effect of the Invention

In the invention, the closed space is formed between the diaphragm part and the measurement portion to be measured by attaching the pressure sensor to the measurement portion using the attaching means. Accordingly, it is possible to measure a pulse wave based on up-and-down motion of a skin surface of the measurement portion resulting from a blood pressure change without pressing a blood vessel, and thus it is possible to continuously measure a pulse wave for a long time.

MODE(S) FOR CARRYING OUT THE INVENTION

Hereinafter, an embodiment of the invention will be described with reference to drawings.

Figure 1:
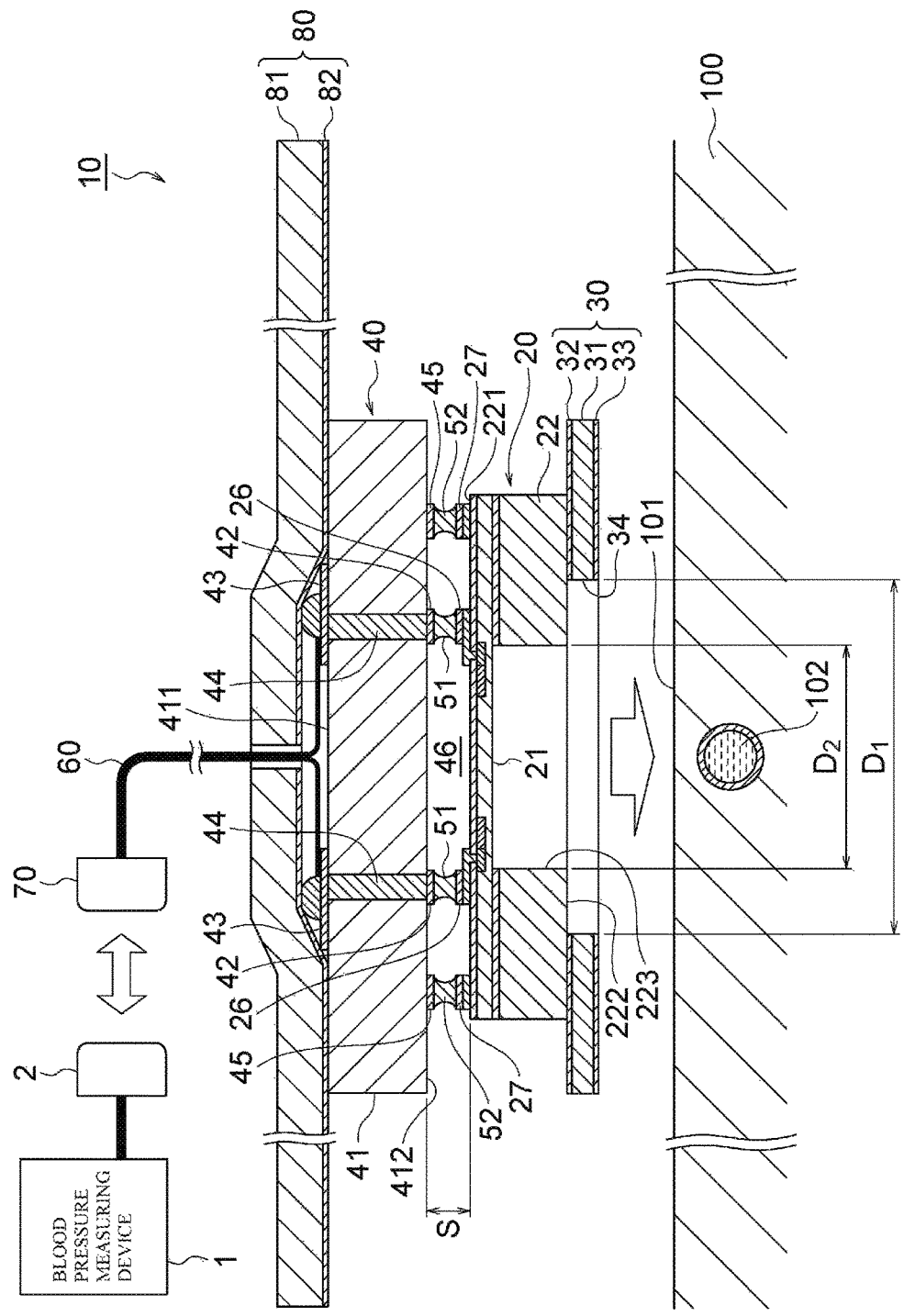
FIG. 1 is a cross-sectional view illustrating a pulse wave sensor unit in an embodiment of the invention.
Figure 2:
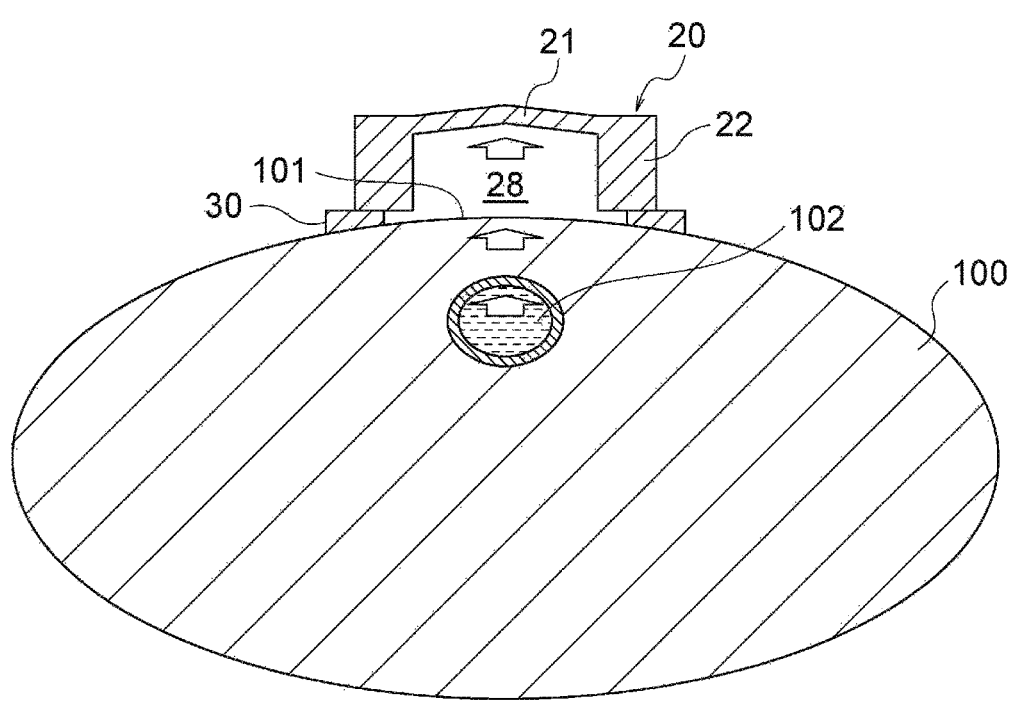
FIG. 2 is a diagram illustrating a principle of pulse wave measurement using the pulse wave sensor unit in the embodiment of the invention.

FIG. 1 is a cross-sectional view illustrating a pulse wave sensor unit in the present embodiment, and FIG. 2 is a diagram illustrating a principle of pulse wave measurement using the pulse wave sensor unit in the present embodiment.

The pulse wave sensor unit 10 in the present embodiment is a sensor unit which measures a blood vessel pulsation waveform (simply referred to as a "pulse wave"), and is used by being connected to a blood pressure measuring device 1 at the time of measuring blood pressure by the blood pressure measuring device 1. As illustrated in FIG. 1, the pulse wave sensor unit 10 includes a pressure sensor 20, a seal member 30, a wiring circuit board 40, connecting parts 51 and 52, a cable 60, a connector 70, and an adhesive tape 80.

When a pulse wave is measured using the pulse wave sensor unit 10, a closed space 28 is formed between a diaphragm part 21 of the pressure sensor 20 and a measurement portion 101 to be measured as illustrated in FIG. 2. Then, a pulse wave is measured by detecting a pressure change on a surface of the measurement portion 101 resulting from a blood pressure change using a piezo-resistor 23 (see FIG. 4) provided in the diaphragm part 21. In order to facilitate understanding of the principle of pulse wave measurement, the wiring circuit board 40, the connecting parts 51 and 52, the cable 60, the connector 70, and the adhesive tape 80 are omitted in FIG. 2.

Hereinafter, a detailed description will be given of a configuration of the pulse wave sensor unit 10 in the present embodiment.

Figure 3:
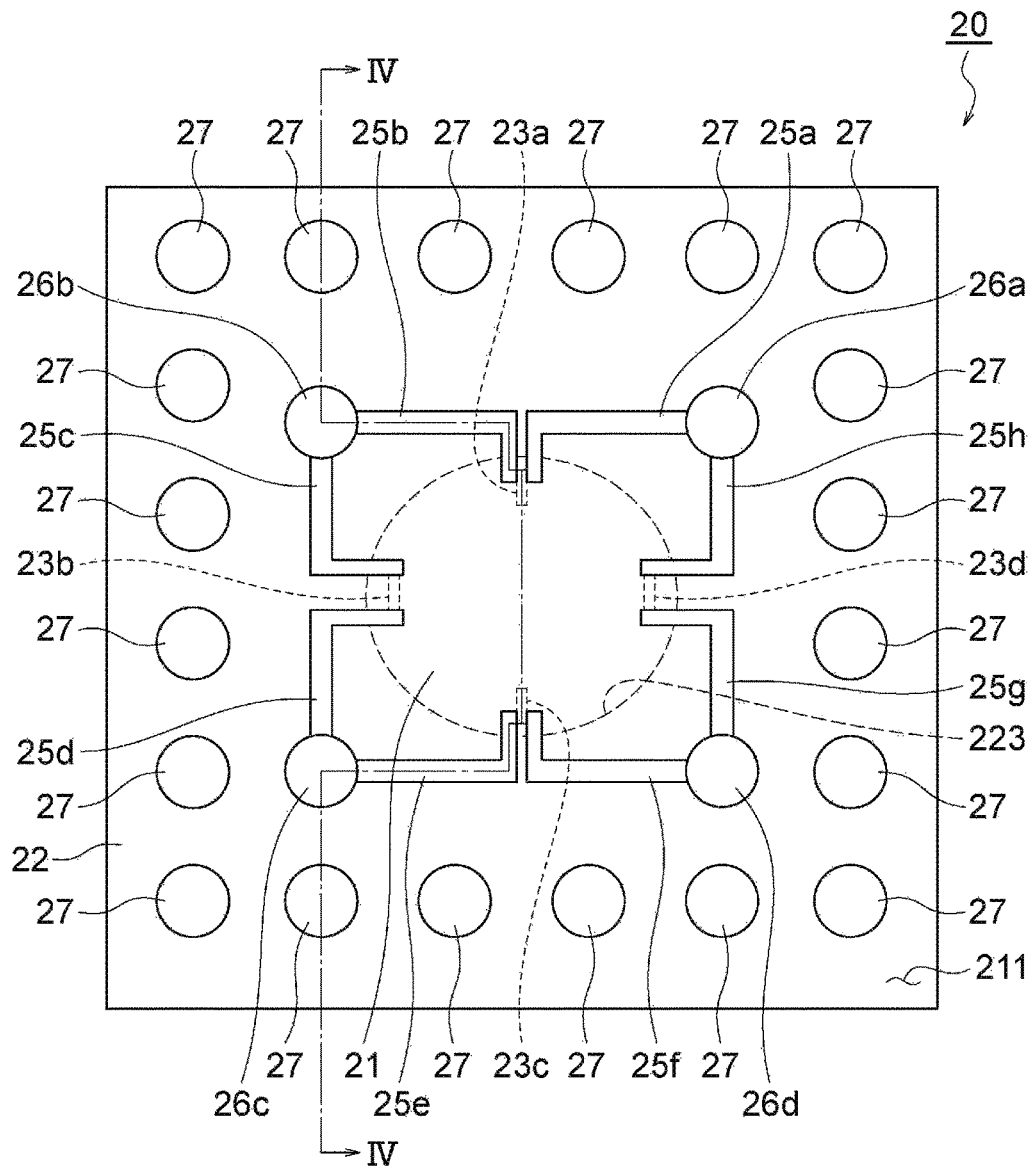
FIG. 3 is a plan view illustrating a pressure sensor in the embodiment of the invention.
Figure 4:
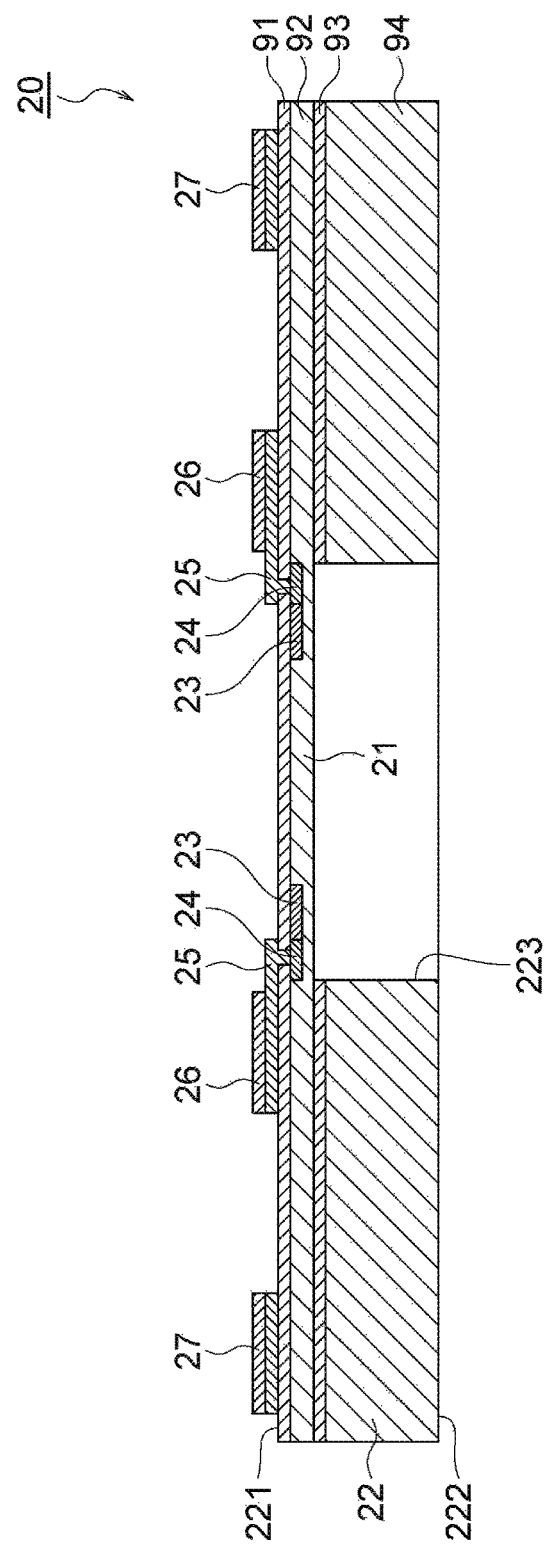
FIG. 4 is a cross-sectional view taken along IV-IV line of FIG. 3.

FIG. 3 is a plan view illustrating the pressure sensor 20 in the present embodiment, and FIG. 4 is a cross-sectional view taken along IV-IV line of FIG. 3.

The pressure sensor 20 is a piezo-resistance type semiconductor pressure sensor using Micro Electro Mechanical Systems (MEMS) technology, and includes the diaphragm part 21 and a support part 22 which supports the diaphragm part 21 as illustrated in FIG. 3 and FIG. 4. In the present embodiment, as illustrated in FIG. 4, the diaphragm part 21 includes a first $SiO_2$ layer 91 and a first silicon (Si) layer 92. Meanwhile, the support part 22 includes first and second $SiO_2$ layers 91 and 93 and first and second Si layers 92 and 94. Configurations of the diaphragm part 21 and the support part 22 are not particularly limited thereto. As illustrated in FIG. 1, in the present embodiment, an upper surface 221 of the support part 22 faces a lower surface 412 of the wiring circuit board 40, and the diaphragm part 21 is close to the lower surface 412 of the wiring circuit board 40. The upper surface 221 of the support part 22 in the present embodiment corresponds to an example of a first main surface in the invention.

As illustrated in FIG. 3 and FIG. 4, the diaphragm part 21 is a circular thin film. The support part 22 includes a cylindrical shape having a circular aperture 223. An outer circumferential edge of the diaphragm part 21 is connected to an upper portion of the aperture 223 of the support part 22, and the diaphragm part 21 is supported by the support part 22. The outer circumferential edge of the diaphragm part 21 is connected to the support part 22 across the whole circumference, and thus the upper portion of the aperture 223 of the support part 22 is airtightly blocked by the diaphragm part 21. Shapes of the diaphragm part 21 and the aperture 223 are not particularly limited to circular shapes.

Four piezo-resistors 23a to 23d are provided in the diaphragm part 21. The piezo-resistors 23a to 23d are disposed around an outer circumference of the diaphragm part 21. The respective piezo-resistors 23a to 23d are electrically connected to first electrodes 26a to 26d through contact parts 24a to 24h and wiring patterns 25a to 25h. The first electrodes 26a to 26d are provided on the upper surface 221 of the support part 22. For example, the piezo-resistors 23a to 23d and the contact parts 24a to 24h are formed by doping the first Si layer 92 included in the diaphragm part 21 with boron (B). Although not particularly illustrated in FIG. 3, the contact parts 24a to 24h are provided between the piezo-resistors 23a to 23d and the wiring patterns 25a to 25h, respectively.

In the present embodiment, as illustrated in FIG. 3, a plurality of first dummy electrodes 27 are provided on the upper surface 221 of the support part 22. The first dummy electrodes 27 are not electrically connected to the piezo-resistor 23, a contact part 24, a wiring pattern 25, a first electrode 26, etc., and are electrodes which do not electrically function. The first dummy electrodes 27 are disposed around an outer circumference of the upper surface 221 of the support part 22, and disposed at substantially equal intervals along the outer circumference. Positions of the first dummy electrodes 27 on the upper surface 221 of the support part 22 are set according to arrangement of the first electrode 26, etc., and are not particularly limited to around the outer circumference of the upper surface 221. Intervals of the first dummy electrodes 27 are not particularly limited to equal intervals.

In the present embodiment, the piezo-resistors 23a to 23d are collectively referred to as the "piezo-resistor 23", the contact parts 24a to 24h are collectively referred to as the "contact part 24", the wiring patterns 25a to 25h are collectively referred to as the "wiring pattern 25", and the first electrodes 26a to 26d are collectively referred to as the "first electrode 26".

As illustrated in FIG. 1, the seal (sealing) member 30, which has an annular shape and is elastically deformable, is attached to the support part 22 of the pressure sensor 20. The seal member 30 is interposed between the pressure sensor 20 and the measurement portion 101, thereby an airtightness of the closed space 28 (see FIG. 2) is improved.

The seal member 30 includes a substrate 31, a first adhesive layer 32, and a second adhesive layer 33. The first and second adhesive layers 32 and 33 are stacked on upper and lower surfaces of the substrate 31, respectively.

The seal member 30 is attached to a lower surface 222 of the support part 22 through the first adhesive layer 32. At the time of measuring blood pressure, the seal member 30 adheres to the measurement portion 101 through the second adhesive layer 33. Accordingly, airtightness of the closed space 28 is further improved.

The substrate 31 of the seal member 30 is made of a material having electrical insulation such as a resin material. For this reason, at the time of measuring blood pressure, noise from a living body is inhibited from being mixed with an output of the pulse wave sensor unit 10, and detection accuracy of the pressure sensor 20 is improved.

Further in the present embodiment, an inner diameter $D_1$ of an inner hole 34 of the seal member 30 is relatively larger than an inner diameter $D_2$ of the aperture 223 of the support part 22 ($D_1 > D_2$), and an inner circumferential edge of the inner hole 34 is relatively positioned on an outer side of an inner circumferential edge of the aperture 223. Accordingly, a measurable area of the pressure sensor 20 is enlarged, and thus the pulse wave sensor unit 10 is easily installed on an arm 100 of a subject at the time of measuring blood pressure.

As illustrated in FIG. 1, the wiring circuit board 40 includes a substrate 41, a second electrode 42, a third electrode 43, and a through-hole 44. The through-hole 44 in the present embodiment corresponds to an example of a conduction path of the invention.

The substrate 41 is made of a material having electric insulation. Examples of a specific material included in the substrate 41 may include a resin material such as polyimide (PI), glass epoxy resin, etc., a glass material, a ceramic material, etc.

The second electrode 42 is provided on the lower surface 412 of the substrate 41. The second electrode 42 is disposed to correspond to the first electrode 26 of the pressure sensor 20 described above. In contrast, the third electrode 43 is provided on an upper surface 411 of the substrate 41. The through-hole 44 penetrates the upper and lower surfaces 411 and 412 of the substrate 41, and electrically connects the second electrode 42 and the third electrode 43 to each other. The lower surface 412 of the substrate 41 in the present embodiment corresponds to an example of a "second main surface" in the invention.

Further, the wiring circuit board 40 in the present embodiment includes second dummy electrodes 45. The second dummy electrodes 45 are not electrically connected to the second electrode 42, the third electrode 43, the through-hole 44, etc., and do not have any electrical function. The second dummy electrodes 45 are provided on the lower surface 412 of the substrate 41, and are disposed to correspond to the first dummy electrodes 27 of the pressure sensor 20 described above.

A configuration of the wiring circuit board 40 is not particularly limited to the above-described configuration. For example, a multi-layer wiring circuit board may be used as the wiring circuit board 40. In this case, pitches of the electrodes 42 and 43 may be converted, or locations of the electrodes 42 and 43 may be changed by forming a via-hole or an internal wire in the multi-layer wiring circuit board, and electrically connecting the second electrode 42 and the third electrode 43 through the via-hole or the internal wire. The via-hole or the internal wire in this case corresponds to an example of the conduction path in the invention.

In the present embodiment, the pressure sensor 20 and the wiring circuit board 40 are mechanically and electrically connected to each other between the first and second connecting parts 51 and 52 while the upper surface 221 of the support part 22 faces the lower surface 412 of the wiring circuit board 40. The first connecting part 51 in the present embodiment corresponds to an example of connecting means in the invention.

Specifically, the first connecting part 51 mechanically and electrically connects the first electrode 26 of the pressure sensor 20 and the second electrode 42 of the wiring circuit board 40 to each other. The second connecting part 52 mechanically connects the first dummy electrodes 27 of the pressure sensor 20 and the second dummy electrodes 45 of the wiring circuit board 40 to each other.

Therefore, in the present embodiment, it is possible to improve mechanical bond strength of the pressure sensor 20 and the wiring circuit board 40 by connecting the first and second dummy electrodes 27 and 45 through the second connecting part 52.

Figure 5:
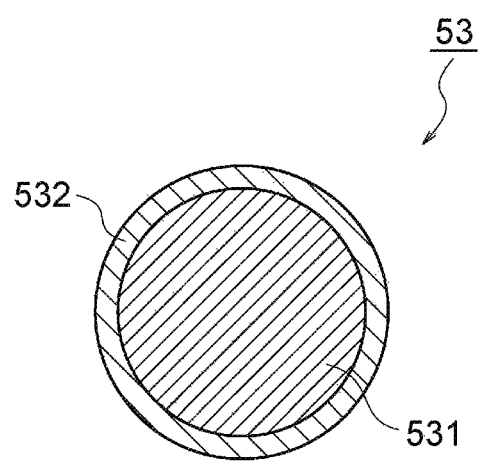
FIG. 5 is a cross-sectional view illustrating, a solder ball used for the pulse wave sensor unit in the embodiment of the invention.

The first and second connecting parts 51 and 52 are formed by melting and then hardening a solder ball 53 illustrated in FIG. 5. The solder ball 53 includes a spherical core (core material) 531 and a solder layer 532 covering an outer circumference of the core 531. A highly heat-resistant resin material having a higher melting point than that of solder included in the solder layer 532 can be used as a material included in the core 531. Specifically, examples of the material may include a divinylbenzene cross-linked polymer. A copper layer, etc. may be interposed between the core 531 and the solder layer 532. FIG. 5 is a cross-sectional view illustrating the solder ball used for the pulse wave sensor unit in the present embodiment. The core 531 of the solder ball 53 may be made of a metal such as copper having a higher melting point than that of solder included in the solder layer 532.

The connecting parts 51 and 52 are formed using the solder ball 53, thereby the pressure sensor 20 and the wiring circuit board 40 can be reliably separated from each other at a predetermined distance S (see FIG. 1). Accordingly, it is possible to reliably ensure a space 46 for allowing deformation of the diaphragm part 21 between the diaphragm part 21 and the wiring circuit board 40, and it is possible to improve detection accuracy of the pressure sensor 20 (see FIG. 1).

The solder ball 53 in the present embodiment corresponds to an example of a solder ball in the invention, the core 531 in the present embodiment corresponds to an example of a core in the invention, and the solder layer 532 in the present embodiment corresponds to an example of a solder layer in the invention.

The first and second connecting parts 51 and 52 may be formed by hardening a conductive adhesive instead of the solder ball 53. Alternatively, the first and second connecting parts 51 and 52 may be formed by a solder ball not having the core 531 instead of the solder ball 53.

Figure 6:
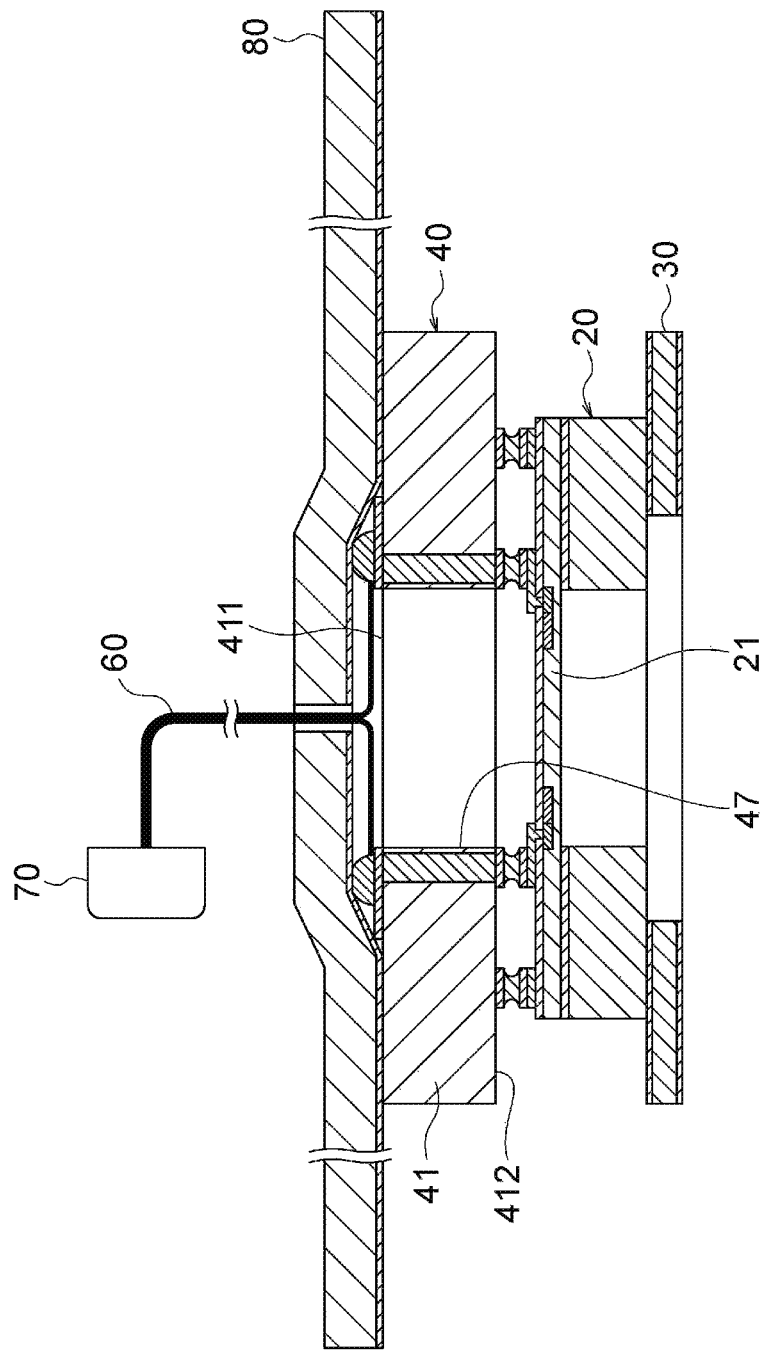
FIG. 6 is a cross-sectional view illustrating a first modified example of the pulse wave sensor unit in the embodiment of the invention.
Figure 7:
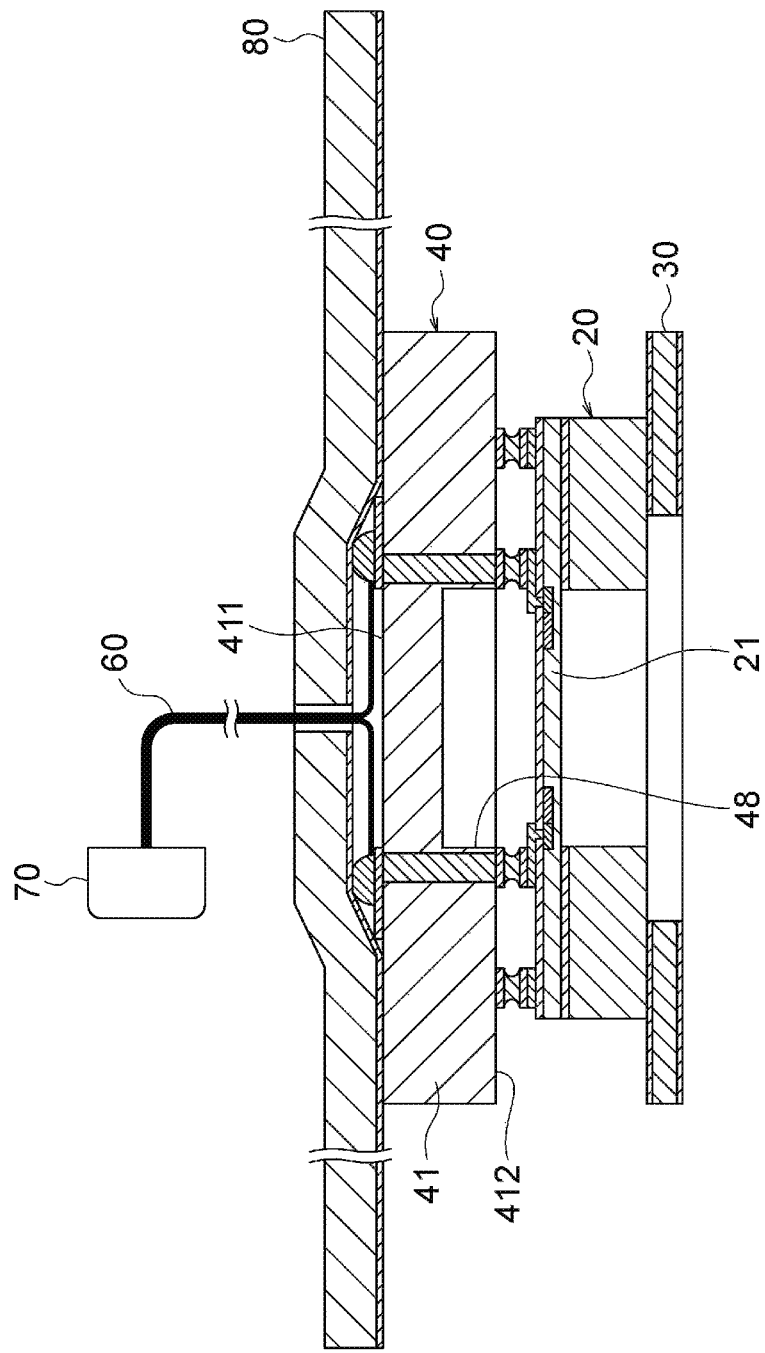
FIG. 7 is a cross-sectional view illustrating a second modified example of the pulse wave sensor unit in the embodiment of the invention.

FIG. 6 is a cross-sectional view illustrating a first modified example of the pulse wave sensor unit in the present embodiment, and FIG. 7 is a cross-sectional view illustrating a second modified example of the pulse wave sensor unit in the present embodiment.

As illustrated in FIG. 6, a through-hole 47 penetrating from the upper surface 411 to the lower surface 412 of the wiring circuit board 40 may be formed at a portion of the wiring circuit board 40 corresponding to the diaphragm part 21. The through-hole 47 has an area required to allow deformation of the diaphragm part 21 such as substantially the same area as that of the diaphragm part 21.

Alternatively, as illustrated in FIG. 7, a depression 48 may be formed at a portion of the lower surface 412 of the wiring circuit board 40 corresponding to the diaphragm part 21. The depression 48 has an area required to allow deformation of the diaphragm part 21 such as substantially the same area as that of the diaphragm part 21.

The through-hole 47 or the depression 48 is formed in the wiring circuit board 40, thereby it is possible to ensure a space for allowing deformation of the diaphragm part 21 even when the predetermined distance S is not ensured between the pressure sensor 20 and the wiring circuit board 40.

Returning to FIG. 1, one end of the cable 60 is connected to the third electrode 43 of the wiring circuit board 40 by soldering, etc. Meanwhile, the other end of the cable 60 is connected to the connector 70. When blood pressure is measured by the blood pressure measuring device 1, the pulse wave sensor unit 10 is electrically connected to the blood pressure measuring device 1 by fitting the connector 70 to a connector 2 of the blood pressure measuring device 1.

The adhesive tape 80 includes a substrate 81 and an adhesive layer 82 provided on a lower surface of the substrate 81. The adhesive tape 80 has a larger area than that of the wiring circuit board 40, and the upper surface 411 of the wiring circuit board 40 is stuck to a portion of the adhesive tape 80. Although not particularly illustrated, release paper may be stuck to an exposed portion of the adhesive layer 82 in the adhesive tape 80.

When an exposed portion of the adhesive layer 82 in the adhesive tape 80 is stuck to the arm 100 of the subject, the wiring circuit board 40 is attached to the arm 100, and the pressure sensor 20 is pressed against the measurement portion 101 through the seal member 30.

The adhesive tape 80 in the present embodiment corresponds to an example of attaching means in the invention. As long as the attaching means has an attaching function of attaching the pressure sensor 20 to the measurement portion 101, the attaching means in the invention is not particularly limited to the adhesive tape 80.

For example, a band-shaped tape having a hook-and-loop fastener, a ring-shaped band having elasticity, a clip, etc. may be used as the attaching means. Alternatively, the closed space 28 may be formed by attaching the pressure sensor 20 to the measurement portion 101 using the second adhesive layer 33 of the seal member 30 described above. In this case, the adhesive tape 80 may be omitted.

When blood pressure is measured by the blood pressure measuring device 1 to which the pulse wave sensor unit 10 described above is connected, first, the wiring circuit board 40 is attaching to the arm 100 of the subject using the adhesive tape 80, and the pressure sensor 20 is pressed against the measurement portion 101 while the pressure sensor 20 faces the measurement portion 101. In this way, the pressure sensor 20 is attached to the measurement portion 101, and the closed space 28 (see FIG. 2) is formed between the diaphragm part 21 of the pressure sensor 20 and the measurement portion 101. Then, the diaphragm part 21 is deformed in association with up-and-down motion of the surface of the measurement portion 101 resulting from a blood pressure change, and the piezo-resistor 23 detects a stress change generated in the diaphragm part 21 as a resistance change, thereby measuring a pulse wave.

For example, specific examples of the measurement portion 101 may include a skin surface of the arm 100 of the subject corresponding to a radial artery 102. An artery as a target of pulse wave measurement by the pulse wave sensor unit 10 is not particularly limited to the radial artery 102, and may be a brachial artery, or an ulna artery, etc. Alternatively, the artery as the target of pulse wave measurement by the pulse wave sensor unit 10 may be an artery of a part other than the arm 100. In this case, a skin surface of the region other than the arm 100 of the subject corresponding to the artery serves as the measurement portion 101.

The blood pressure measuring device 1 including a computer, a display, etc. acquires a voltage value indicating a pulse wave from the pulse wave sensor unit 10 through the connectors 70 and 2, etc., converts the pulse wave voltage value into a blood pressure value, and displays the blood pressure value.

As described in the foregoing, in the present embodiment, the pressure sensor 20 is attached to the measurement portion 101 by the adhesive tape 80, thereby the closed space 28 is formed between the diaphragm part 21 and the measurement portion 101. Accordingly, it is possible to measure a pulse wave based on up-and-down motion of the skin surface of the measurement portion 101 resulting from a blood pressure change without pressing a blood vessel, and thus it is possible to continuously measure a pulse wave for a long time.

In the present embodiment, the pressure sensor 20 is directly mounted on the wiring circuit board 40, and thus it is possible to miniaturize the pulse wave sensor unit 10 and to reduce the number of components. As a result, it is possible to reduce the cost of the pulse wave sensor unit 10. For this reason, the pulse wave sensor unit 10 may be disposable, and hygiene is improved.

In the present embodiment, the seal member 30 directly sticks to the pressure sensor 20, and the seal member 30 directly comes into contact with the measurement portion 101. Accordingly, in the present embodiment, it is possible to miniaturize the pulse wave sensor unit 10 and to reduce the number of components. As a result, it is possible to reduce the cost of the pulse wave sensor unit 10, and thus it is possible to obtain a structure more suitable for disposable use.

Further, in the present embodiment, the connector 70 is included, and can be attached to and detached from the blood pressure measuring device 1. In the present embodiment, since the connector 70 is included, a power source or a circuit may not be provided in the pulse wave sensor unit 10 in comparison with a case in which the pulse wave sensor unit and the blood pressure measuring device are connected through radio communication. For this reason, in the present embodiment, it is possible to obtain a structure more suitable for disposable use.

Further, in the present embodiment, the pressure sensor 20, the wiring circuit board 40, and the adhesive tape 80 are unitized (integrated), and thus it is possible to rapidly and easily attach the pulse wave sensor unit 10 to the measurement portion 101.

The above-described embodiment has been described to facilitate understanding of the invention, and has not been described to restrict the invention. Therefore, each element disclosed in the above-described embodiment is intended to include all changes of design or equivalents belonging to a technical scope of the invention.

EXPLANATIONS OF LETTERS OR NUMERALS

1 . . . blood pressure measuring device
  2 . . . connector
  10 . . . pulse wave sensor unit
  20 . . . pressure sensor
    21 . . . diaphragm part
    22 . . . support part
      221 . . . upper surface
      222 . . . lower surface
      223 . . . aperture
    23, 23a to 23d . . . piezo-resistor
    24, 24a to 24h . . . contact part
    25, 25a to 25h . . . wiring pattern
    26, 26a to 26d . . . first electrode
    27 . . . first dummy electrode
    28 . . . closed space
  30 . . . seal member
    31 . . . substrate
    32 . . . first adhesive layer
    33 . . . second adhesive layer
    34 . . . inner hole
  40 . . . wiring circuit board
    41 . . . substrate 411 . . . upper surface
412 . . . lower surface
42 . . . second electrode
43 . . . third electrode
44 . . . through-hole
45 . . . second dummy electrode
46 . . . space
47 . . . through-hole
48 . . . depression
51 . . . first connecting part
52 . . . second connecting part
53 . . . solder ball
531 . . . core
532 . . . solder layer
60 . . . cable
70 . . . connector
80 . . . adhesive tape
81 . . . substrate
82 . . . adhesive layer
91 . . . first $SiO_2$ layer
92 . . . first Si layer
93 . . . second $SiO_2$ layer
94 . . . second Si layer
100 . . . arm of subject
101 . . . measurement portion
102 . . . radial artery

What is claimed is:

1. A pulse wave sensor unit comprising:
a blood pressure pulse wave pressure sensor;
a fastener that attaches the blood pressure pulse wave pressure sensor to a measurement portion that generates measurable blood pressure pulse waves, and
an annular seal which is interposed between the blood pressure pulse wave pressure sensor and the measurement portion, wherein
the blood pressure pulse wave pressure sensor includes:
  a diaphragm that includes a detector and uninterruptedly faces the measurement portion, the detector detecting deformation of the diaphragm, and
  an annular support which supports the diaphragm and integrally formed with the diaphragm, the annular support comprising:
    an aperture for allowing the diaphragm to face the measurement portion,
    an inner surface, and
    an outer surface exposed to an outside, wherein:
the annular seal is directly attached to the annular support and directly contacts the measurement portion,
a closed space defined by the inner surface is formed between the diaphragm and the measurement portion during the measurement of the measurement portion and when the blood pressure pulse wave pressure sensor is attached to the measurement portion by the fastener,
the diaphragm is deformed by up-and-down motion of the blood pressure pulse waves generated by the measurement portion via fluid transmitted within the closed space, and
the blood pressure pulse wave pressure sensor is separated from the measurement portion during measurement of the measurement portion, detects deformation of the diaphragm, and generates a pulse wave voltage from the generated blood pressure pulse waves.

2. The pulse wave sensor unit according to claim 1, further comprising a wiring circuit board on which the blood pressure pulse wave pressure sensor is mounted.

3. The pulse wave sensor unit according to claim 2, further comprising an electromechanical connector which mechanically and electrically connects the wiring circuit board and the blood pressure pulse wave pressure sensor, wherein
the wiring circuit board and the blood pressure pulse wave pressure sensor face each other through the electromechanical connector.

4. The pulse wave sensor unit according to claim 3, wherein
a gap is formed between the diaphragm and the wiring circuit board.

5. The pulse wave sensor unit according to claim 4, wherein
the gap is formed by the electromechanical connector.

6. The pulse wave sensor unit according to claim 3, wherein
the blood pressure pulse wave pressure sensor includes:
  a piezo-resistor which is provided in the diaphragm; and
  a first electrode which is provided on a first main surface of the support facing the wiring circuit board and is electrically connected to the piezo-resistor,
the wiring circuit board includes a second electrode which is provided on a second main surface facing the blood pressure pulse wave pressure sensor, and
the electromechanical connector electrically connects the first electrodes and the second electrodes.

7. The pulse wave sensor unit according to claim 6, wherein
the electromechanical connector includes a solder ball, and
the solder ball includes:
  a core; and
  a solder layer which covers the core.

8. The pulse wave sensor unit according to claim 6, further comprising:
a cable which has one end connected to the wiring circuit board; and
a cable connector which is connected to the other end of the cable.

9. The pulse wave sensor unit according to claim 8, wherein
the wiring circuit board includes:
  a third electrode which is provided on an opposite surface to the second main surface, and
  a conduction path which electrically connects the second electrode and the third electrode, and
the cable is connected to the third electrode.

10. The pulse wave sensor unit according to claim 1, wherein the annular support extends below and supports the diaphragm.

* * * * *